United States Patent
Monzani et al.

(10) Patent No.: US 9,540,461 B2
(45) Date of Patent: Jan. 10, 2017

(54) FLUORINATED UNSATURATED COMPOUND AND POLYMERS OBTAINABLE THEREFROM

(75) Inventors: Cristiano Monzani, Trezzo sull'Adda (IT); Vito Tortelli, Milan (IT)

(73) Assignee: SOLVAY SPECIALTY POLYMERS ITALY S.P.A., Bollate (Milan) (IT)

( * ) Notice: Subject to any disclaimer, the term of this patent is extended or adjusted under 35 U.S.C. 154(b) by 0 days.

(21) Appl. No.: 14/128,045

(22) PCT Filed: Jun. 15, 2012

(86) PCT No.: PCT/EP2012/061432
§ 371 (c)(1),
(2), (4) Date: Dec. 20, 2013

(87) PCT Pub. No.: WO2013/000735
PCT Pub. Date: Jan. 3, 2013

(65) Prior Publication Data
US 2014/0142239 A1    May 22, 2014

(30) Foreign Application Priority Data

Jun. 27, 2011 (EP) .................................. 11171434

(51) Int. Cl.
| | | |
|---|---|---|
| *C08F 14/18* | (2006.01) | |
| *C08F 14/22* | (2006.01) | |
| *C08F 14/28* | (2006.01) | |
| *C07C 381/00* | (2006.01) | |
| *C08F 2/22* | (2006.01) | |
| *C08F 214/18* | (2006.01) | |
| *C07C 313/10* | (2006.01) | |
| *C08F 14/26* | (2006.01) | |
| *C08F 216/14* | (2006.01) | |

(52) U.S. Cl.
CPC ............. *C08F 14/28* (2013.01); *C07C 313/10* (2013.01); *C07C 381/00* (2013.01); *C08F 2/22* (2013.01); *C08F 14/18* (2013.01); *C08F 14/22* (2013.01); *C08F 14/26* (2013.01); *C08F 214/18* (2013.01); *C08F 214/186* (2013.01); *C08F 216/1408* (2013.01)

(58) Field of Classification Search
USPC .............................. 526/243; 524/544; 558/62
See application file for complete search history.

(56) References Cited

U.S. PATENT DOCUMENTS

| | | | | |
|---|---|---|---|---|
| 3,627,799 A | * | 12/1971 | Young et al. ................. | 558/281 |
| 4,292,449 A | * | 9/1981 | Krespan ....................... | 568/649 |
| 4,633,082 A | * | 12/1986 | Sauers .......................... | 250/282 |
| 5,891,965 A | | 4/1999 | Worm et al. | |
| 2008/0033164 A1 | * | 2/2008 | Syvret .................. | C01B 21/086 540/145 |
| 2011/0303121 A1 | * | 12/2011 | Geim ..................... | B82Y 30/00 106/287.28 |

FOREIGN PATENT DOCUMENTS

| | | |
|---|---|---|
| WO | 0024709 A2 | 5/2000 |
| WO | 0146108 A1 | 6/2001 |
| WO | WO-2009/083451 A1 * | 7/2009 |

OTHER PUBLICATIONS

Krespan, G. et al., Perfluoroallylfluorosulfate, a reactive new perfluoroalkylating agent, J. Am. Chem. Soc., vol. 103, pp. 5598-5599 (1981).*

Carlson P. et al., "Organic Fluoropolymers; Ullmann's Encyclopedia of Industial Chemistry", Article first published online: Jun. 15, 2000, p. 495-533—Wiley-VCH Verlag, Weinhein, DE—DOI: 10.1002/14356007.a11_393.

Krespan G. et al., "Perfluoroallylfluorosulfate, a reactive new perfluoroallylating agent", J. Am. Chem. Soc., 1981, vol. 103, pp. 5598-5599—American Chemical Society.

Kostov G.K. et al., "Study on the synthesis of perfluorovinyl-sulfonic functional monomer and its copolymerization with tetrafluoroethylene", Journal of Applied Polymer Science, Jan. 20, 1993, vol. 47, No. 4, pp. 735-741, XP055018879, John Wiley & Sons, Inc., New York, NY, US ISSN: 0021-8995, DOI: 10.1002/app.1993.070470417.

Du L. et al., "Synthesis of pentafluorosulfanyl trifluorovinyl ether and Its facile rearrangement to difluoro (pentafluorosulfanyl)acetyl fluoride", Angewandte Chemie, International Edition, Jul. 27, 2007, vol. 46, No. 35, pp. 6626-6628, XP055018863, Wiley-VCH Verlag, Weinhem, DE ISSN: 1433-7851, DOI: 10.1002/anie.200702425.

* cited by examiner

*Primary Examiner* — Peter D Mulcahy
*Assistant Examiner* — Henry Hu

(57) ABSTRACT

A compound of formula $CF_2=CFCF_2OSF_5$ and polymers comprising recurring units deriving from $CF_2=CFCF_2OSF_5$ are disclosed as well as processes for their preparation.

16 Claims, No Drawings

FLUORINATED UNSATURATED COMPOUND AND POLYMERS OBTAINABLE THEREFROM

This application is a U.S. national stage entry under 35 U.S.C. §371 of International Application No. PCT/EP2012/061432 filed Jun. 15, 2012, which claims priority to European Application No. 11171434.1, filed Jun. 27, 2011. The entire contents of these applications are explicitly incorporated herein by this reference.

TECHNICAL FIELD

The present invention relates to a novel fluorinated unsaturated compound of formula $CF_2=CFCF_2OSF_5$, to a process for its preparation and to the polymers obtainable therefrom.

BACKGROUND ART

The use of fluorinated unsaturated compounds comprising side groups, e.g. fluorinated vinyl ethers, as monomers in the preparation of fluorinated polymers has been extensively described; see for instance CARLSON, Peter, et al. Organic Fluoropolymers; Ullmann's Encyclopedia of Industial Chemistry. Weinheim: Wiley-VCH Verlag, 2005.

So far the use of fluorinated unsaturated compounds comprising the $-OSF_5$ moiety has not been described. It has now been found that pentafluorosulfanyl fluoroallylether, $CF_2=CFCF_2OSF_5$, can be prepared from readily available starting materials and that it can polymerize providing polymers comprising $-OSF_5$ groups.

SUMMARY OF INVENTION

A first object of the present invention is a compound of formula (I): (I) $CF_2=CFCF_2OSF_5$.

Compound of formula (I), pentafluorosulfanyl fluoroallylether, is a liquid at room temperature, with a boiling point of 56° C.

Compound of formula (I) may be prepared by reaction of $SOF_4$ with fluoroallyl fluorosulfate, $CF_2=CFCF_2OSO_2F$, in the presence of a suitable fluoride catalyst.

Fluoride catalysts suitable in the reaction are alkali metal fluorides, alkali-earth metal fluorides, quaternary ammonium fluorides and silver fluoride. Preferred fluoride catalysts are CsF, KF, RbF, LiF, NaF, $CaF_2$, $BaF_2$, $MgF_2$, $SrF_2$, AgF. Most preferred metal fluorides are CsF and KF.

Catalyst concentration is not critical and amounts of catalysts are determined by the environment in which the reaction is carried out.

$SOF_4$ may be added to the reaction in an equimolar amount with respect to fluoroallyl fluorosulfate but typically it is added in a slight excess. Typical molar ratios of $SOF_4$ with respect to fluoroallyl fluorosulfate are for instance 1.3:1 or even 1.2:1.

The reaction is generally carried out in liquid phase, either in the absence or in the presence of an organic solvent inert under the reaction conditions. When no solvent is added, the fluoroallyl fluorosulfate itself advantageously provides for a liquid reaction medium. Non-limiting examples of suitable organic solvents are for instance glymes, e.g. diethylenglycol diethylether, chlorofluorocarbons, perfluorocarbons, e.g. $CF_3CF_2CF_3$, perfluoroethers, e.g. $CF_3OCF_2CF_3$, chlorofluoroethers, e.g. $CF_3OCFClCClF_2$ or perfluoropolyethers.

The reaction between $SOF_4$ and fluoroallyl fluorosulfate is generally carried out at a temperature from −150 to 50° C., preferably from −100° C. to 40° C., more preferably from −50° C. to 30° C.

Reaction pressure is not a critical parameter. Reaction pressure is generally atmospheric pressure.

At the end of the reaction $CF_2=CFCF_2OSF_5$ can be separated from the solvent (if any) and from any residual fluoroallyl fluorosulfate and recovered using for instance conventional distillation techniques, either at standard pressure or under vacuum.

Compound of formula (I) has been found to readily polymerize in the presence of a suitable polymerization initiator.

Accordingly a further object of the present invention is a polymer comprising recurring units deriving from $CF_2=CFCF_2OSF_5$.

In one embodiment the polymer consists of recurring units deriving from $CF_2=CFCF_2OSF_5$.

In another embodiment the polymer comprises recurring units deriving from $CF_2=CFCF_2OSF_5$ and recurring units deriving from at least one other ethylenically unsaturated monomer copolymerizable therewith.

The expression "monomer copolymerizable therewith" is used herein to refer to compounds capable to be converted into polymers by combination with $CF_2=CFCF_2OSF_5$.

Within the context of the present invention the expression "at least one" when referred to a "monomer" is intended to denote one or more than one monomer(s). Mixtures of monomers can be advantageously used for the preparation of the polymers of the invention.

The at least one ethylenically unsaturated monomer may be selected from fluorinated and/or non-fluorinated monomers.

The expression "fluorinated" is used herein to refer to compounds (e.g. compounds, polymers, monomers etc.) that are either totally or partially fluorinated, i.e. wherein all or only a part of the hydrogen atoms have been replaced by fluorine atoms. Analogously, the expression "non-fluorinated" is used herein to refer to compounds that do not contain any fluorine atoms.

Non-limiting examples of suitable ethylenically unsaturated fluorinated monomers are:
  $C_2$-$C_8$ fluorofluoroolefins, such as tetrafluoroethylene, hexafluoropropylene, pentafluoropropylene, and hexafluoroisobutylene;
  $C_2$-$C_8$ hydrogenated fluoroolefins, such as vinyl fluoride, 1,2-difluoroethylene, vinylidene fluoride and trifluoroethylene;
  fluoroalkylethylenes of formula $CH_2=CH-R_{f0}$, wherein $R_{f0}$ is a $C_1$-$C_6$ fluoroalkyl or a $C_1$-$C_6$ fluorooxyalkyl having one or more ether groups;
  chloro- and/or bromo- and/or iodo-$C_2$-$C_6$ fluoroolefins, like chlorotrifluoroethylene;
  fluoroalkylvinylethers of formula $CF_2=CFOR_{f1}$ in which $R_{f1}$ is a $C_1$-$C_6$ fluoroalkyl, e.g. $-CF_3$, $-C_2F_5$, $-C_3F_7$;
  hydrofluoroalkylvinylethers of formula $CH_2=CFOR_{f1}$ in which $R_{f1}$ is a $C_1$-$C_6$ fluoroalkyl, e.g. $-CF_3$, $-C_2F_5$, $-C_3F_7$;
  fluoro-oxyalkylvinylethers of formula $CF_2=CFOR_{O1}$, in which $R_{O1}$ is a $C_1$-$C_{12}$ alkyl, or a $C_1$-$C_{12}$ fluoroalkyl having one or more ether groups, like perfluoro-2-propoxy-propyl;
  fluoroalkyl-difluoromethoxy-vinylethers of formula $CF_2=CFOCF_2OR_{f2}$ in which $R_{f2}$ is a $C_1$-$C_6$ fluoroalkyl, e.g. —$CF_3$, —$C_2F_5$, —$C_3F_7$ or a $C_1$-$C_6$ fluoroalkyloxy having one or more ether groups, like —$C_2F_5$—O—$CF_3$;

functional fluoro-alkylvinylethers of formula $CF_2$=$CFOY_0$, in which $Y_0$ is a $C_1$-$C_{12}$ alkyl or fluoroalkyl, or a $C_1$-$C_{12}$ alkyloxy, or a $C_1$-$C_{12}$ fluoroalkyloxy, said $Y_0$ group having one or more ether groups and $Y_0$ comprising a carboxylic or sulfonic acid group, in its acid, acid halide or salt form;

fluorodioxoles, of formula:

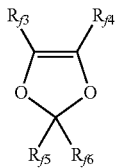

wherein each of $R_{f3}$, $R_{f4}$, $R_{f5}$, $R_{f6}$, equal or different each other, is independently a fluorine atom, a $C_1$-$C_6$ fluoro- or (halo)fluoroalkyl, optionally comprising one or more oxygen atom, e.g. —$CF_3$, —$C_2F_5$, —$C_3F_7$, —$OCF_3$, —$OCF_2CF_2OCF_3$.

Non-limiting examples of suitable ethylenically unsaturated non-fluorinated monomers are:

$C_2$-$C_8$ olefins, such as ethylene and propylene;

$C_2$-$C_8$ chloroolefins, such as vinyl chloride, 1,2-dichloroethylene, vinylidene chloride;

acrylic- or methacrylic monomers of formula $CH_2$=$CR_{h1}R_{h2}$ in which $R_{h1}$ is chosen from hydrogen and the methyl group and $R_{h2}$ is the —CO—$R_{h3}$ group in which $R_{h3}$ is chosen from the —OH group, the —O—$R_{h4}$ groups with $R_{h4}$ chosen from the linear or branched alkyl groups containing from 2 to 18 carbon atoms optionally bearing one or more —OH group.

Mixtures of fluorinated and non-fluorinated monomers may be used to prepare polymers comprising recurring units deriving from $CF_2$=$CFCF_2OSF_5$. Non-limiting examples of ethylenically unsaturated non-fluorinated monomers suitable to be used in admixture with fluorinated monomers are ethylene and propylene.

When the polymer comprises in addition to recurring units deriving from $CF_2$=$CFCF_2OSF_5$ also recurring units deriving from at least one non-fluorinated monomer, the total amount of recurring units deriving from said at least one non-fluorinated monomer is typically of at most 50 mole %, preferably of at most 40 mole %.

Preferably the at least one ethylenically unsaturated fluorinated monomer copolymerizable with $CF_2$=$CFCF_2OSF_5$ is selected from the group consisting of the fluorinated monomers as detailed above.

More preferably the ethylenically unsaturated fluorinated monomer copolymerizable with $CF_2$=$CFCF_2OSF_5$ is selected from the group consisting of:

$C_2$-$C_8$ fluoroolefins, preferably tetrafluoroethylene and/or hexafluoropropylene;

$C_2$-$C_8$ hydrogenated fluoroolefins, such as vinyl fluoride, 1,2-difluoroethylene, vinylidene fluoride and trifluoroethylene;

chloro- and/or bromo- and/or iodo-$C_2$-$C_6$ fluoroolefins, like chlorotrifluoroethylene and/or bromotrifluoroethylene;

fluoroalkylvinylethers of formula $CF_2$=$CFOR_{f1}$ in which $R_{f1}$ is a $C_1$-$C_6$ fluoroalkyl, e.g. —$CF_3$, —$C_2F_5$, —$C_3F_7$;

fluoro-oxyalkylvinylethers of formula $CF_2$=$CFOR_{O1}$, in which $R_{O1}$ is a $C_1$-$C_{12}$ fluoroalkyl having one or more ether groups, like perfluoro-2-propoxy-propyl.

Even more preferably the ethylenically unsaturated fluorinated monomer copolymerizable with $CF_2$=$CFCF_2OSF_5$ is selected from the group consisting of:

$C_2$-$C_8$ fluoroolefins, preferably tetrafluoroethylene and/or hexafluoropropylene;

$C_2$-$C_8$ hydrogenated fluoroolefins, preferably vinylidene fluoride and/or trifluoroethylene;

fluoroalkylvinylethers of formula $CF_2$=$CFOR_{f1}$ in which $R_{f1}$ is a $C_1$-$C_6$ fluoroalkyl, e.g. —$CF_3$, —$C_2F_5$, —$C_3F_7$.

When the polymer comprises recurring units deriving from at least one ethylenically unsaturated monomer other than $CF_2$=$CFCF_2OSF_5$, the amount of recurring units deriving from $CF_2$=$CFCF_2OSF_5$ may range from 0.1 to 99.9 mole %, typically from 1 to 90 mole %, more typically from 1 to 50 mole %.

The polymers comprising recurring units deriving from $CF_2$=$CFCF_2OSF_5$ may be semi-crystalline or amorphous, depending on the nature of the at least one ethylenically unsaturated monomer polymerized with $CF_2$=$CFCF_2OSF_5$ and on the molar composition of the polymer.

In a first embodiment the polymer comprises recurring units deriving from $CF_2$=$CFCF_2OSF_5$ and recurring units deriving from at least tetrafluoroethylene.

In a second embodiment the polymer comprises recurring units deriving from $CF_2$=$CFCF_2OSF_5$ and recurring units deriving from at least vinylidene fluoride. Advantageously these polymers may additionally comprise recurring units deriving from hexafluoropropylene.

Polymers comprising recurring units deriving from $CF_2$=$CFCF_2OSF_5$ can be prepared by any of the known processes for making fluorinated polymers.

Such process may be conducted in aqueous or non-aqueous liquid medium, the latter including fluorinated solvents and carbon dioxide, as well as in mixed media as known in the art.

The process may, for example, be suspension polymerization, solution polymerization, emulsion polymerization or bulk polymerization.

In a first embodiment the process is an emulsion polymerization process, typically an emulsion polymerization process carried out in an aqueous medium in the presence of a surfactant.

Suitable surfactants are for instance anionic fluorinated surfactants, for example salts of fluorinated carboxylic acids or of sulfonic acids, having a perfluoropolyether or perfluorocarbon structure or partially fluorinated, cationic surfactants, for example quaternary ammonium fluorinated salts, or even fluorinated non ionic surfactants. The above surfactants can be also used in mixtures.

Non limiting examples of surfactants having a perfluorocarbon structure are for instance ammonium or alkaline metal salts of $C_8$-$C_{10}$ perfluorcarboxylic acids or perfluorooxycarboxylates of formula $R_sO$—$CF_2CF_2$—O—$CF_2$—$COOX_a$ wherein $R_s$ is a perfluoro(oxy)alkyl group, and $X_a$ is H, a monovalent metal or an ammonium group of formula $NR^N_4$, with $R^N$, equal or different at each occurrence, being H or a $C_{1-6}$ hydrocarbon group. Non limiting examples of surfactants having a perfluoropolyether structure are for instance selected from those with formula $F_2ClOC(CF_2CF(CF_3)O)_p(CF_2O)_qCF_2COOR'$ wherein R'=H, Na, K, $NH_4$, p/q=10. Generally these fluorinated surfactant(s) have an average molecular weight in the range 500-700.

Alternative non limiting examples of suitable anionic fluorinated surfactants are for instance surfactants complying with formula (II) below:

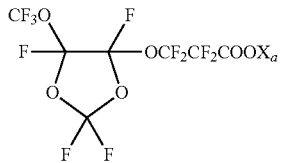

wherein $X_a$ is as defined above.

Generally the process is a radical polymerization process wherein monomers are polymerized in the presence of a radical polymerization initiator.

Any initiator or initiator system suitable for radical polymerization may be used in the present invention. Non limiting examples of suitable radical initiators are for instance organic initiators selected among bis(fluoroacyl) peroxides, bis(chlorofluoroacyl)peroxides, dialkyl peroxydicarbonates, diacyl peroxides, peroxyesters, azo compounds or inorganic initiators such as ammonium and/or potassium and/or sodium persulphate, optionally in combination with ferrous, cuprous or silver salts or a redox system such as ammonium persulphate/disulfite and potassium permanganate.

Alternatively the polymers of the invention may be obtained by polymerizing the selected monomers with a radical photoinitiator in the presence of visible-UV radiation, either in suspension or in emulsion in water.

The polymerization system may optionally comprise small amounts of auxiliaries such as buffers, complex-formers, chain transfer agents or perfluorinated oils.

The polymerization can be carried out at any suitable pH. pH is typically not critical and it depends on the initiator system used.

Polymerization conditions are not particularly limited and will depend on the monomers. Polymerization pressure is typically from 0.1 to 10 MPa, preferably from 0.5 to 5 MPa.

At the end of the polymerization process the polymer may be recovered using any conventional polymer recovery technique as well known in the art.

The dried polymer may then be subjected to conventional post-treatment and pelletization procedures. For instance, the polymer may be subjected to a fluorination treatment to remove unstable chain-end groups as known in the art.

The polymers comprising recurring units deriving from $CF_2\!\!=\!\!CFCF_2OSF_5$ can be used in any application in which fluoropolymers are typically employed, including but not limited to the production of films, hoses, pipes, tubings, cables, wire insulations, fittings, molded seals and gaskets, o-rings, bearings, coatings (e.g. architectural coatings, protective coatings), fibers, filtration membranes.

The following examples are given only for illustrative purposes and are not limitative of the present invention.

Should the disclosure of any patents, patent applications, and publications which are incorporated herein by reference conflict with the description of the present application to the extent that it may render a term unclear, the present description shall take precedence.

Where the concentration of all but one of the monomers is specified, the concentration of the remaining monomer can be deduced by subtraction of the known constituents from 100 mole %, that is, the total mole % of the copolymer.

EXAMPLES

Raw Materials

Fluoroallyl fluorosulfate was synthesized according to previously described techniques (KRESPAN, G, et al. Perfluoroallylfluorosulfate, a reactive new perfluoroallylating agent. *J. Am. Chem. Soc.* 1981, vol. 103, p. 5598-5599.) and obtained with a selectivity of 80% (on converted $SO_3$) as a fluid having boiling point of 64° C.

Characterization

NMR: spectra were recorded on a Varian Inova 400 spectrometer operating at 376.198 MHz for $^{19}F$ and a Varian S 500 MHz spectrometer operating at 470.300 MHz for $^{19}F$ and 125.70 MHz for $^{13}C$. $^{19}F$ NMR and $^{13}C$ NMR spectra of the monomer were recorded in acetone at room temperature and the spectra was referenced to $CFCl_3$. $^{19}F$ NMR of the polymers were recorded in $C_6F_6$ at 60° C. and the spectra were referenced to the solvent ($C_6F_6$, −164.67 ppm).

Wurzschmitt Digestion

About 50 mg of the polymer sample was mixed with 0.2 g of ethylene glycol, 6 g of sodium peroxide and 0.2 g of sodium carbonate. The mixture was heated up with a flame in a closed combustion device (Wurzschmitt bomb) for 1 h 30'. After cooling the residue was dissolved in 200 ml of distilled water, boiled and allowed to cool down again. After appropriate dilution the solution was subjected to the analysis by ionic chromatography in order to determine quantitatively the sulphur content of the polymer.

An ion chromatograph (ICS3000 DIONEX) with an ion-exchange column (AS 14A), a suppressor (ASRS 300) and a conductivity detector was used. The mobile phase consisted of 8 mM sodium carbonate and 1 mM sodium bicarbonate. The flow rate was 1 ml/min.

Transition temperatures (Melting and Glass transition temperature) were determined by DSC at a heating rate of 20° C./min following the procedure of ASTM D3418-08.

Weight Loss Determination

The weight loss determination at 200° C. was carried out using a TGA PYRIS 1 equipment from Perkin-Elmer according to method ASTM E 1131. A 10 mg sample of the polymer was subjected to constant heating in air at a rate of 10° C./min from 23° C. up to 750° C. The temperature at which 2% and 10% weight loss are measured is given.

Example 1

Synthesis of $CF_2\!\!=\!\!CFCF_2OSF_5$ (I)

In an AlS1-316 reactor having 300 ml volume, equipped with magnetic stirring, was charged 9.3 g of previously dried KF and 100 ml of anhydrous diethylenglycol diethylether. The reactor was evacuated at reduced pressure, cooled at −196° C. before introducing 22.3 g of $SOF_4$. The reactor was warmed at 0° C. under stirring, cooled again at −196° C. and 35 g of fluoroallyl fluorosulfate was charged. The reactor mixture was allowed to return to 0° C. and kept at 0° C. for 3.5 h under vigorous stirring, then at 20° C. for another 0.5 h. The reactor was connected to two consecutive traps maintained at −78° C., opened and evacuated at reduced pressure. 43.1 g of crude product were collected in the two traps. After distillation in a Spalthror Fischer apparatus (60 plates efficiency) 30 g of $CF_2\!\!=\!\!CFCF_2OSF_5$ (I) were collected with a purity of 99.5%.

$^{19}F$ NMR($CFCl_3$ reference): +70.5 ppm (m; 4F; —F$\underline{S}F_4$); +63.2 ppm (m; 1F; —$\underline{F}SF_4$); −74.3 ppm (ddqd; 2F; —OC F₂—); −91.2 ppm (ddt; 1F; C$\underline{F}$₂═CF—); −104.5 ppm (ddt; 1F; CF₂═C$\underline{F}$—); −192.8 ppm (ddt; 1F; CF₂═C$\underline{F}$—).

¹³C NMR: 154.7 ppm (td; 1C; $\underline{C}$F₂═C$\underline{F}$—); 121.8 ppm (m; 1C; C$\underline{F}$₂═CF—); 117.2 ppm (td; 1C; —OCF₂—).

Example 2

Polymer Comprising Recurring Units of (I) and Vinylidene Fluoride (CH₂═CF₂)—Bulk Polymerization In an AISI-316 reactor having 45 ml volume, equipped with magnetic stirring, 300 μl of perfluoropropionylperoxide (0.098M in CF₃OCFClCF₂Cl), 8.98 mmoles of (I) and 14.06 mmoles of vinylidene fluoride were introduced. The reactor was evacuated at −196° C., and then brought to room temperature. The cooling-evacuation procedure was repeated twice. At the end of the degassing procedure the reactor was maintained at 25° C. under stirring. The internal pressure decreased from 0.69 MPa to 0.23 MPa (in about 70 hours). After distillation of the unreacted monomers, the polymer was treated at 150° C. under vacuum for three hours and 2.56 g of a transparent and colourless polymer were obtained.

¹⁹F-NMR analysis carried out at 60° C. on the polymer dissolved in C₆F₆ showed the following signals: +72.5 ppm (—FS$\underline{F}$4); +60.5 ppm (—$\underline{F}$SF₄); −80 ppm (—C$\underline{F}$₂OSF₅); −90/−120 ppm (Rf—C$\underline{F}$₂—Rf—; Rf—C$\underline{F}$₂—Rh; Rh—C$\underline{F}$₂—Rh); −182 ppm (—C$\underline{F}$₂C$\underline{F}$—(C$\underline{F}$₂OSF₅)—Rf).

The molar percentage of CF₂═CFCF₂OSF₅ in the polymer as determined by NMR was determined to be 36 mole %.

The polymer was analyzed also with the Wurzschmitt digestion according to the procedure described above. The molar percentage of CF₂═CFCF₂OSF₅ in the polymer obtained from this method was determined to be 35 mole %.

Example 3

Polymer Comprising Recurring Units of (I) and Vinylidene Fluoride (VDF)—Emulsion Polymerization In the reactor of Example 2, 4.8 g of an emulsion prepared with distilled water, Fluorolink® PFPE monocarboxylate ammonium salt (FLK 7850) (7% by weight) and 0.0211 g of ammonium persulfate, 5.33 mmoles of (I) and 27.27 mmoles of VDF were sequentially introduced. The reactor was cooled to −196° C., evacuated, and then allowed to return to room temperature. The cooling-evacuation procedure was repeated twice. At the end of the degassing procedure the reactor temperature was brought to 65° C. and held at the same temperature for 19 hours under stirring while the internal pressure was allowed to decrease from 1.03 MPa to 0 MPa. The reactor was cooled down to room temperature, the emulsion discharged and coagulation induced by addition of concentrated HNO₃ (65%). The polymer was separated from the liquid phase, washed with distilled water, treated at 150° C. under vacuum for three hours: 2.10 g of a solid polymer were isolated.

¹⁹F-NMR analysis carried out at 60° C. on the polymer dissolved in C₆F₆ showed the following signals: +72.5 ppm (—FS$\underline{F}$₄); +60.5 ppm (—$\underline{F}$SF₄); −80 ppm (—C$\underline{F}$₂OSF₅); −90/−120 ppm (Rf—C$\underline{F}$₂—Rf—; Rf—C$\underline{F}$₂—Rh; Rh—C$\underline{F}$₂—Rh); −182 ppm (—CF₂C$\underline{F}$—(CF₂OSF₅)—Rf). The molar percentage, determined by NMR analysis, of CF₂═CFCF₂OSF₅ in the polymer was determined to be 16.7 mole %.

Example 4

Polymer Comprising Recurring Units of (I) and Tetrafluoroethylene (TFE)—Bulk Polymerization Following the same procedure of Example 2, 300 μl of perfluoropropionylperoxide (0.098M in CF₃OCFClCF₂Cl) and 8.76 mmoles of (I) were sequentially introduced into the reactor. At the end of the degassing procedure 19.6 mmoles of TFE were introduced. The reactor temperature was maintained at 25° C. and the internal pressure was allowed to decrease from 0.95 MPa bar to 0.27 MPa bar (in about 50 hours). 2.02 g of a white crystalline polymer were obtained.

Due to the low solubility, the polymer was analyzed with the Wurzschmitt digestion. The molar percentage of CF₂═CFCF₂OSF₅ in the polymer was determined to be 5 mole %.

Example 5

Polymer Comprising Recurring Units of (I) and Tetrafluoroethylene (TFE)—Emulsion Polymerization Following the same procedure of Example 3, 3.5 g of an emulsion prepared with distilled water, Fluorolink® PFPE monocarboxylate ammonium salt (FLK 7850) (7% by weight), 0.0132 g of ammonium persulfate and 3.25 mmoles of (I) were sequentially introduced in the reactor. At the end of the degassing procedure 9.9 mmoles of TFE were introduced. The internal pressure was allowed to decrease from 0.40 MPa to 0.05 MPa (about 21 hours). The reactor was cooled at room temperature and the solid recovered as described in Example 3, providing 0.80 g of a solid polymer.

Due to the low solubility, the polymer was analyzed with the Wurzschmitt digestion. The molar percentage of CF₂═CFCF₂OSF₅ in the polymer was determined to be 16 mole %.

Example 6

Polymer Comprising Recurring Units of (I), Vinylidene Fluoride (VDF) and Hexafluoropropylene (HFP)

Following the same procedure of Example 3, 11.8 g of an emulsion prepared with distilled water, Fluorolink® PFPE monocarboxylate ammonium salt (FLK 7850) (7% by weight), 0.033 g of ammonium persulfate, 5.55 mmoles of (I), 16.42 mmoles of VDF and 5.47 mmoles of HFP were sequentially introduced in the reactor. At the end of the degassing procedure the reactor temperature was brought to 65° C. and the internal pressure allowed decreasing from 0.68 MPa to 0 MPa (about 22 hours). The reactor was cooled to room temperature and the solid recovered as described in Example 3, providing 3.23 g of a white rubbery material.

¹⁹F-NMR analysis carried out at 60° C. on the polymer dissolved in C₆F₆ showed the following signals: +72.5 ppm (—FS$\underline{F}$₄); +60.5 ppm (—$\underline{F}$SF₄); −70/−76 ppm (—CF₂CF—(C$\underline{F}$₃)—Rh; —CF₂CF—(C$\underline{F}$₃)—Rf); −80 ppm (—C$\underline{F}$₂OSF₅); −90/−120 ppm (Rf—C$\underline{F}$₂—Rf—; Rf—C$\underline{F}$₂—Rh; Rh—C$\underline{F}$₂—Rh); −182 ppm (—CF₂C$\underline{F}$—(CF₂OSF₅)—Rf; —CF₂C$\underline{F}$—(CF₃)—Rf).

The molar percentage of each monomer in the polymer was determined by NMR analysis with the following results: $CF_2=CFCF_2OSF_5$: 20.4 mole %, VDF: 59.7 mole %, HFP: 19.9 mole %.

The properties of the polymers of Examples 2-6 are reported in Table 1.

TABLE 1

| Ex. | Monomer (mole %) | | | | Melting temp. ($2^{nd}$ heating) (° C.) | 2% weight loss (° C.) | 10% weight loss (° C.) |
|---|---|---|---|---|---|---|---|
| | (I) | VDF | TFE | HFP | | | |
| 2 | 36 | 64 | | | — | 427 | 444 |
| 3 | 16.7 | 83.3 | | | 130 | 398 | 443 |
| 4 | 5 | | 95 | | 275-323 | 456 | 487 |
| 5 | 16 | | 84 | | — | 409 | 451 |
| 6 | 20.4 | 59.7 | | 19.9 | — | 403 | 443 |

Polymers comprising recurring units deriving from (I) and VDF may be both amorphous (Example 2) and semi-crystalline (Example 3).

The same has been observed for polymers comprising recurring units deriving from (I) and TFE (Examples 5 and 4 respectively).

All the polymers obtained are stable at high temperatures with a weight loss of less than 2 wt % up to about 400° C. and less than 10% up to about 450° C.

The invention claimed is:

1. A compound of formula $CF_2=CFCF_2OSF_5$.

2. Process for the preparation of the compound of claim 1 comprising reacting $SOF_4$ with $CF_2=CFCF_2OSO_2F$ in the presence of a fluoride catalyst.

3. A polymer comprising recurring units derived from $CF_2=CFCF_2OSF_5$.

4. Polymer according to claim 3 further comprising recurring units derived from at least one ethylenically unsaturated monomer.

5. Polymer according to claim 4 wherein the ethylenically unsaturated monomer is selected from a fluorinated monomer and/or a non-fluorinated monomer.

6. Polymer according to claim 5 wherein the fluorinated monomer is selected from the group consisting of: $C_2$-$C_8$ fluorofluoroolefins; $C_2$-$C_8$ hydrogenated fluoroolefins; fluoroalkylethylenes of formula $CH_2=CH-R_{f0}$, wherein $R_{f0}$ is a $C_1$-$C_6$ fluoroalkyl or a $C_1$-$C_6$ fluorooxyalkyl having one or more ether groups; chloro- and/or bromo- and/or iodo-$C_2$-$C_6$ fluoroolefins; fluoroalkylvinylethers of formula $CF_2=CFOR_{f1}$ in which $R_{f1}$ is a $C_1$-$C_6$ fluoroalkyl; hydrofluoroalkylvinylethers of formula $CH_2=CFOR_{f1}$ in which $R_{f1}$ is a $C_1$-$C_6$ fluoroalkyl; fluorooxyalkylvinylethers of formula $CF_2=CFOR_{O1}$, in which $R_{O1}$ is a $C_1$-$C_{12}$ alkyl or a $C_1$-$C_{12}$ fluoroalkyl having one or more ether groups; fluoroalkyl-difluoromethoxy-vinylethers of formula $CF_2=CFOCF_2OR_{f2}$ in which $R_{f2}$ is a $C_1$-$C_6$ fluoroalkyl or a $C_1$-$C_6$ fluoroalkyloxy having one or more ether groups; functional fluoro-alkylvinylethers of formula $CF_2=CFOY_0$, in which $Y_0$ is a $C_1$-$C_{12}$ alkyl or fluoroalkyl, or a $C_1$-$C_{12}$ alkyloxy, or a $C_1$-$C_{12}$ fluoroalkyloxyl, said $Y_0$ group having one or more ether groups and $Y_0$ comprising a carboxylic or sulfonic acid group, in its acid, acid halide or salt form; and fluorodioxoles of formula:

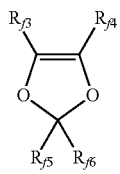

wherein each of $R_{f3}$, $R_{f4}$, $R_{f5}$, $R_{f6}$, equal or different each other, is independently a fluorine atom, a $C_1$-$C_6$ fluoro- or (halo)fluoroalkyl, optionally comprising one or more oxygen atom.

7. Polymer according to claim 5 wherein the non-fluorinated monomer is selected from the group consisting of: $C_2$-$C_8$ olefins; $C_2$-$C_8$ chloroolefins; acrylic- or methacrylic monomers of formula $CH_2=CR_{h1}R_{h2}$ in which $R_{h1}$ is chosen from hydrogen and the methyl group and $R_{h2}$ is the $-CO-R_{h3}$ group in which $R_{h3}$ is chosen from the $-OH$ group and the $-O-R_{h4}$ groups with $R_{h4}$ chosen from the linear or branched alkyl groups containing from 2 to 18 carbon atoms optionally bearing one or more $-OH$ group.

8. Polymer according to claim 4 wherein the ethylenically unsaturated monomer is a fluorinated monomer selected from tetrafluoroethylene, hexafluoropropylene, vinylidene fluoride, trifluoroethylene, and fluoroalkylvinylethers of formula $CF_2=CFOR_{f1}$ wherein $R_{f1}$ is $-CF_3$, $-C_2F_5$, or $-C_3F_7$.

9. Polymer according to claim 4, wherein the polymer comprises recurring units derived from $CF_2=CFCF_2OSF_5$ and recurring units derived from tetrafluoroethylene.

10. Polymer according to claim 9, wherein the polymer further comprises recurring units derived from hexafluoropropylene.

11. Polymer according to claim 4, wherein the polymer comprises recurring units derived from $CF_2=CFCF_2OSF_5$ and recurring units derived from vinylidene fluoride.

12. Polymer according to claim 11, wherein the polymer further comprises recurring units derived from hexafluoropropylene.

13. Polymer according to claim 3, wherein the amount of recurring units derived from $CF_2=CFCF_2OSF_5$ ranges from 0.1 to 99.9 mole %.

14. Process for the preparation of a polymer of claim 3 comprising the step of polymerizing the compound of formula $CF_2=CFCF_2OSF_5$ and optionally at least one ethylenically unsaturated monomer in the presence of a polymerization initiator.

15. Process according to claim 14 wherein the polymerization initiator is a radical polymerization initiator.

16. An article comprising the polymer of claim 3.

* * * * *